United States Patent [19]

Favara et al.

[11] 4,189,606

[45] Feb. 19, 1980

[54] 13-AZAPROSTAGLANDINS

[75] Inventors: Duccio Favara, Como; Umberto Guzzi, Milan, both of Italy

[73] Assignee: Gruppo Lepetit S.p.A., Milan, Italy

[21] Appl. No.: 22,766

[22] Filed: Mar. 22, 1979

Related U.S. Application Data

[62] Division of Ser. No. 765,039, Feb. 2, 1977.

[30] Foreign Application Priority Data

Feb. 23, 1976 [GB] United Kingdom ............... 7043/76

[51] Int. Cl.$^2$ ........................................... C07C 177/00
[52] U.S. Cl. .................................................... 562/455
[58] Field of Search ......................................... 562/455

[56] References Cited

U.S. PATENT DOCUMENTS 4,033,996  7/1977  Cragoe et al. ..................... 260/490

Primary Examiner—Robert Gerstl

[57] ABSTRACT

Prostaglandin derivatives wherein the atom at the position 13 of the lower side-chain is replaced by nitrogen. The new compounds have abortifacient activity.

1 Claim, No Drawings

13-AZAPROSTAGLANDINS

CROSS-REFERENCE TO RELATED APPLICATIONS

This is a divisional of application Ser. No. 765,039, filed Feb. 2, 1977.

BACKGROUND OF THE INVENTION

Prostaglandins having a carbon atom replaced by nitrogen are disclosed in U.S. Pat. No. 3,973,566, U.S. Pat. No. 3,975,399 and in Tetrahedron Letters No. 43, 3853, 1976. In these cases however the substitutions occur at the cyclopentane ring moiety (position 8 and 12), while the side chains are unmodified. The derivatives disclosed in the prior art are to be considered as pirrole and pirazole derivatives, while the invention compounds still pertain to cyclopentane series.

SUMMARY OF THE INVENTION

This invention relates to novel prostaglandin-like compounds and a process for their preparation. The new compounds are 13-azaprostaglandins analogs of the general formula

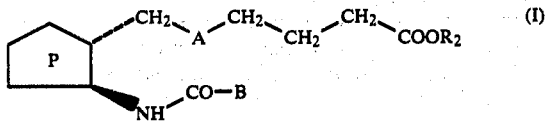

wherein the five membered ring P represents one of the following groups

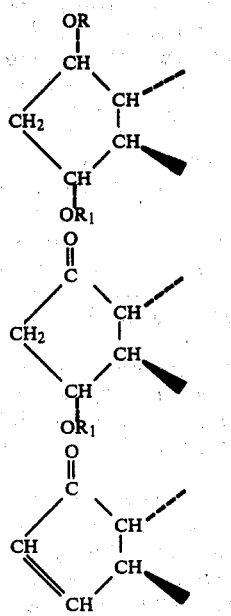

wherein R and $R_1$ are independently selected from hydrogen, and a protecting group of the hydroxy function such as lower alkanoyl of 2 to 5 carbons, benzoyl and tetrahydropyran-2-yl.

The symbol A represents a group —$CH_2$—$CH_2$— or cis —CH=CH—;

The symbol $R_2$ represents hydrogen, alkyl of 1 to 6 carbon atoms or a cation.

The symbol B represents:

(a) a group —X—$R_3$ wherein X is selected from O, S, and NH, and $R_3$ is a straight or branched alkyl of 1 to 7 carbon, a group phenyl-$(CH_2)_n$—, a group substituted phenyl-$(CH_2)_n$—, wherein n is an integer from 0 to 4.

(b) A group —W—$R_3$ wherein $R_3$ has the same meaning as before and W is selected from

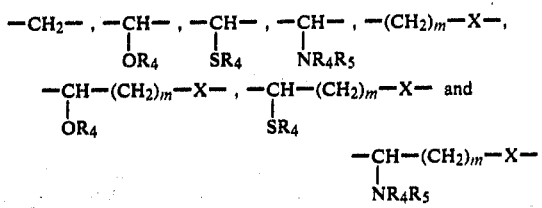

wherein $R_4$ and $R_5$ are independently hydrogen or alkyl of 1 to 6 carbon atoms, m is an integer from 1 to 3 and X has the same meaning as above.

In the formula I above the broken lines represents bonds which extend behind the plane of the paper (α-configuration) while the thickened lines represent bonds which extend out the plane of the paper (b-configuration).

The expression "alkyl of 1 to 6 carbon atoms" when not otherwise specified identifies a straight or branched alkyl radical such as for example methyl, ethyl, propyl, isopropyl, butyl, isobutyl, tert-butyl, pentyl or hexyl. Examples of "straight or branched alkyl of 1 to 7 carbon atoms" are the groups: methyl, ethyl, propyl, isopropyl, isobutyl, tert-butyl, pentyl, isopentyl, hexyl, isohexyl, heptyl, 2,3-dimethyl-butyl, 1-methyl-pentyl, 2-methyl-pentyl, 3-methyl-pentyl, 3,3-trimethyl-butyl, 1,4-dimethyl-pentyl, 1-methylhexyl, 2-methyl-hexyl, 3-methyl-hexyl, 4-methyl-hexyl, and 5-methyl-hehexyl.

"Lower alkanoyl of 2 to 5 carbons" are for instance acetyl, propionyl, butiryl, isobutiryl, pentanoyl and pivaloyl.

The term "cation" identifies a pharmaceutically acceptable non toxic cation such as for instance $Na^+$, $Ca^{++}$, or an organic ammonium cation. With the term "ammonium cation" it is inteded the group $NH_4^+$ as well as non toxic cations derived from organic amines.

The term "substituted phenyl" identifies a phenyl radical substituted by one or two groups selected from methyl, methoxy, nitro, bromo, chloro, fluoro, cyano and trifluoromethyl.

The new compounds are useful as abortifacient agents.

The compounds of the invention may be prepared from a compound of the formula II by following general methods which leads first to azaprostaglandins of the F series, i.e. having the structure (a) for the ring P. These azaprostaglandins may be further transformed into the corresponding derivatives of the series E and A, wherein ring P has respectively the structures (b) and (c). These transformation are easily performed by employing procedures which are well known in the prostaglandins chemistry.

The new compounds of the formula I represent prostaglandin-like structures which, depending on the meaning assumed by the symbol B, contains an urethan, thiourethan, urea, or amide portion in the lower side-chain.

The process for manufacturing the compounds of the formula I involves the utilization as the starting compounds of the isocyanate of the formula II

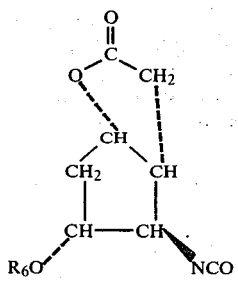

(II)

wherein R$_6$O is a protected hydroxy group such as alkanoyloxy of 2 to 5 carbon atoms, benzoyloxy and tetrahydropyran-2-yloxy. The above isocyanate of formula II may be transformed directly into the corresponding derivatives wherein the portion —NCO is replaced by the group —NH—CO—B wherein the symbol B has the same meanings as before, with the only exception that when in the portion B a group

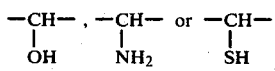

is involved, said group is protected. Any kind of projecting groups of the hydroxy, amino or sulfhydryl function which may be compatible with the further reaction steps and which may be readily removed under mild conditions are suitable for this scope. For instance, benzyl, benzhydryl, trityl, tetrahydropyran-2-yl, lower alkanoyl, lower alkoxy carbonyl, and benzyloxy carbonyl groups may be employed to protect hydroxy and sulfhydryl portions while lower alkanoyl, lower alkoxy carbonyl, benzyloxy carbonyl, succinyl and phthaloyl groups may be employed to protect amino portions. Alternatively, the isocyanate may be converted to the corresponding amine i.e. a compound (hereinafter defined as "the amine") of the formula II wherein the portion —NCO is replaced by —NH$_2$, and then, this latter may be transformed into the corresponding derivative wherein the group amino is replaced by —N-H—CO—B wherein B has the same meanings as before. According to the reaction steps outlined above are obtained lactone intermediates of the formula III.

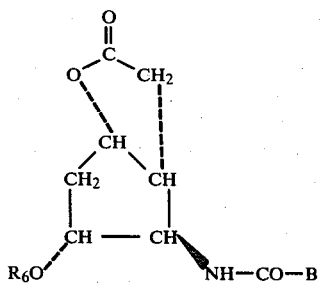

(III)

wherein R$_6$O, and B have the same meanings as described before with the proviso that when in the portion B groups such as

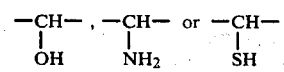

are involved, they are protected as previously described. The further steps leading to compound of formula I consist in reducing the lactone moiety to lactol and subsequent inserting of the upper side-chain according to the common procedures of prostaglandin chemistry.

DESCRIPTION OF SOME PREFERRED EMBODIMENTS

According to the procedures outlined above, the first step of the synthetic route leading to compounds of the formula III wherein B is a group —X—R$_3$ (i.e., urethans, thiourethans and ureas), is carried out by contacting the isocyanate II with a suitable reagent of the formula HX—R$_3$ wherein X is —O—, —S— or —NH— and R$_3$ is a straight or branched alkyl of 1 to 7 carbon atoms, phenyl-(CH$_2$)$_n$— or substituted phenyl-(CH$_2$)$_n$— wherein n is an integer from 0 to 4.

The reaction, although it is not strictly necessary, is preferably carried out in the presence of an organic inert solvent, at a temperature which may vary between the room temperature and the boiling temperature of the reaction mixture, depending on the specific reactivity of the compound of the formula HX—R$_3$ toward the isocyanate group. In some instances the presence of a base as the catalyst may speed up the reaction course. Tertiary organic bases such as lower trialkyl amines or pyridine may be advantageously employed.

The mutual proportion of the reagents is not strictly controlling the operability of the process, although it is preferred to employed about equimolecalar proportions of both reactants.

The specific procedure for preparing compounds of the formula III wherein B is a group W—R$_3$ (i.e. amides), involves reaction between the isocyanate II and a carboxylic acid of the formula HOCO—B wherein B has the same meanings as before, provided that if in the portion B the group hydroxy, amino and mercapto is present, it must be protected during the condensation step. Also in this case it is preferred to carry out the reaction in the presence of an organic inert solvent at a temperature between the room temperature and the boiling temperature of the reaction mixture depending on the reactivity of the carboxylic reagent toward the isocyanate. Tertiary organic amines such as lower trialkyl amines and pyridine are usefully employed as catalytic agents. Pyridine has the advantage to act both as a solvent and as a catalyst.

Both reagents are preferably employed in equal molecular proportions although it is not necessary to follow stoichiometric conditions. A little excess of the carboxylic reactant over the isocyanate may be advantageously employed.

According to an alternative procedure mentioned before, the isocyanate II may be transformed into the corresponding amine by heating with aqueous acids such as for instance aqueous acetic acid. Further reaction of the amine with a carbonyl compound of the formula HOCO—B wherein B has the general meanings described before or a derivative thereof wherein the carboxylic function is activated by appropriate functionalization (acid anhydrides, acid clorides, and so on) gives the corresponding compound of the formula III wherein R$_6$O and B are defined as before. If the portion B involves the presence of unsubstituted hydroxy, sulfhydryl, or amino functions these must be protected during the reaction between amine and the carbonyl compounds. Reaction of the amine with an isocyanate of the formula R$_3$—NCO gives compounds III wherein B is a group —X—R$_3$, wherein X is a group —NH— and R$_3$ has the same meaning as before. The lactones III are then converted to lactols by following standard procedures described in the literature. (E. J. Corey and coworkers, J. Am. Chem. Soc. 91, 5695, 1969; C. Gandolfi and coworkers, Tetrah. Lett. 42, 4307, 1972); the lactol is then condensed with suitable Wittig reagents derived from pentanoic acid and such as for instance, (4-carboxy-butyl)-triphenyl-phosphonium bromide or the corresponding C$_1$-C$_6$ lower alkyl esters, to give the corresponding derivatives of the formula I wherein the ring P has the structure (a) and R is hydrogen, R$_1$ is lower alkanoyl of 2 to 5 carbon atoms, benzoyl or tetrahydropyran-2-yl, R$_2$ is hydrogen or alkyl of 1 to 6 carbon atoms and, if present, the hydroxy, amino or mercapto functions in the portion B are protected.

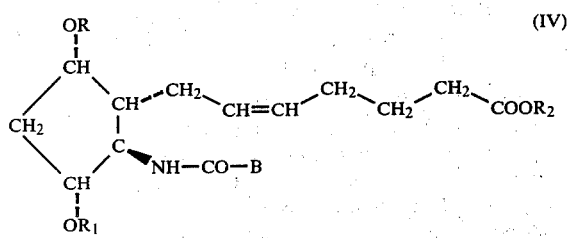

The above product may be submitted to further different reactions to obtain other derivatives of the formula I falling within the scope of this invention. Oxidation of the hydroxy group on the cyclopentane ring (—OR, R=H) to oxo leads to derivatives of the E series (structure b) while a further α,β-elimination of R$_1$OH in the cyclopentane ring yields derivatives of the A series (structure e). Cleavage of the protecting groups, if present, allows restoration of hydroxy, amino, or sulfhydryl functions in the molecule IV or its transformation derivatives.

If desired the free hydroxy group in the position 9 of the prostaglandin skeleton of the derivative indicated above (IV), may be transformed by reaction with alkanoyl and benzoyl halides or anhydrides or by reaction with dihydropyrane into the corresponding acyloxy or tetrahydroxypyranyloxy function. The carboxylic function in the upper chain may be easily converted into the corresponding acid salts by reaction with suitable cation providing reagents such as for instance sodium and calcium hydroxydes, carbonates and bicarbonates or organic amines.

To assess abortifacient activity, female Syrian Golden hamsters weighing 110–150 g were employed. The animals were mated and the presence of the sperm in the vagina was taken as evidence of mating. The day sperm was detected and considered as day one of pregnancy. The azaprostaglandins soluble in water at the test concentration were dissolved in phosphate buffer at pH 7.4. The azaprostaglandins not soluble in water were dissolved in dimethylsulfoxide (DMSO). The volume of the solvent was 2 ml per kilogram of body weight for the buffer and 1 ml per kilogram of body weight for the D.M.S.O.

The animals were treated subcutaneously on day 4 to 6 of pregnancy and were autopsied on day 10 of pregnancy. The uteri were examined for evidence of pregnancy. Animals with at least a live fetus with or without resorption of implantation sites were considered as pregnant. As a parameter for evaluation of abortifacient activity the percentage of pregnant hamsters was considered.

The following table shows the results of some representative azaprostaglandins.

| Compound of Example No. | Doses mg/kg per day s.c. | pregnant treated | % pregnant |
| --- | --- | --- | --- |
| Ex. 30 (more polarisomer) | 1 | 0/6 | 0 |
|  | 0.75 | 3/14 | 21.4 |
|  | 0.5 | 9/11 | 81.8 |
|  | 0.25 | 5/5 | 100 |
| Example 34 (less polarisomer) | 1 | 1/12 | 8 |
|  | 0.5 | 6/17 | 15 |
|  | 0.25 | 6/9 | 66.6 |
|  | 0.125 | 5/5 | 100 |
| Example 34 (more polarisomer) | 0.25 | 1/15 | 6.7 |
|  | 0.125 | 5/17 | 17.4 |
|  | 0.062 | 9/20 | 45 |
|  | 0.031 | 9/10 | 90 |
| Example 38 (less polarisomer) | 0.4 | 2/5 | 40 |
|  | 0.2 | 9/11 | 81.8 |
| Example 38 (more polarisomer) | 0.4 | 1/6 | 16.6 |
|  | 0.2 | 5/11 | 45.5 |
| Example 39 (more polarisomer) | 0.5 | 0/8 | 0 |
|  | 0.1 | 4/4 | 100 |
|  | 0.05 | 6/6 | 100 |

The following Examples described in detail how some representative compounds of the invention may be manufactured.

EXAMPLE 1

Preparation of 2-oxa-6-carbonylazido-7-acetoxy-byciclo[3.3.0]octane-3-one

To a vigorously stirred slurry of 2-oxa-6-carboxy-7-acetoxy-byciclo[3.3.0]octane-3-one (4.56 g, 0.02 moles) in acetone (30 ml) triethylamine (2.22 g, 0.022 moles) in acetone (5 ml) is added at −20° C. To the resulting clear solution ethyl chloroformate (2.61 g. 0.024 moles) is added dropwise at −20° C. After 20 minutes, sodium azide (1.7 g. excess) dissolved in water (10 ml) is added very rapidly at −30° C. The reaction mixture is stirred for one hour at −20° C. and then is poured into ice water (150 ml). After three extractions with benzene the combined extracts are washed with water, dried (MgSO$_4$) and evaporated in vacuo to give the title compound as an oil (3.8 g, 75% yield).

This material being unstable is used immediately without any further purification.

I.R., (neat): 2160, 1780, 1745, 1720 (cm$^{-1}$).

N.M.R. (CDCl$_3$), δ values: 2.05 (s); 2.1–3.3 (m); 5.0–5.3 (m); 5.3–5.6 (m).

EXAMPLE 2

Preparation of 2-oxa-6-isocyanato-7-acetoxy-byciclo[3.3.0]octane-3-one.II,(R$_6$=acetyl)

A solution of 2-oxa-6-carbonylazido-7-acetoxy-byciclo[3.3.0]octane-3-one (3.8 g, 0.015 moles) in dry toluene (15 ml) is added dropwise to boiling dry toluene.

Vigorous evolution of nitrogen occurs. After 20 minutes the solvent is removed in vacuo giving the title compound as an oil (3.36 g, 99% yield). This material being very sensitive to moisture is used immediately without any further purification.

I.R. (neat): 2260, 1780, 1745 (cm$^{-1}$).

N.M.R. (CDCl$_3$), δ values: 2.05 (s); 2.2–3.0 (m); 3.9–4.1 (m); 4.9–5.3 (m).

EXAMPLE 3

Preparation of III (B=—X—R$_3$; X=O; R$_3$=n-pentyl; R$_6$=acetyl)

To a boiling solution of 2-oxa-6-isocyanato-7-acetoxy-byciclo[3.3.0]octane-3-one (675 mg, 3 m.moles) in dry toluene 1-pentanol (1 g excess) in dry toluene is added.

After one minute the solvent is removed in vacuo giving the title compound as an oil which crystallizes on standing. For analytical purposes a sample is crystallized from isopropyl ether. M.P. 76°–77° C.

[α]$_D^{25}$ = −28 (C=1%, chloroform).

Analysis for C$_{15}$H$_{23}$NO$_6$. Calc. C, 57.49; H, 7.40; N, 4.47. Found C, 57.26; H, 7.62; N, 4.63.

EXAMPLE 4

Preparation of III (B=—X—R$_3$; X=O; R$_3$=n-pentyl; R$_6$=hydrogen)

To a solution of III (B=—X—R$_3$; X=O; R$_3$=n-pentyl; R$_6$=acetyl) (500 mg, 0.0016 moles) in dry methanol (30 ml) dry potassium carbonate (200 mg) is added. After 30 minutes citric acid (250 mg) is added and most of the solvent is evaporated in vacuo. Brine is added and the solution is extracted twice with ethyl acetate.

After drying (MgSO$_4$) the solvent is removed in vacuo.

The title compound is crystallized from ether. M.P. 119° C.

[α]$_D^{25}$ = −7 (C=1%, chloroform).

Analysis for C$_{13}$H$_{21}$NO$_5$. Calc. C, 57.55; H, 7.80; N, 5.16. Found C, 57.75; H, 8.02; N, 5.30.

EXAMPLE 5

Preparation of III (B=—X—R$_3$; X=O; R$_3$=n-pentyl; R$_6$=tetrahydropyran-2-yl)

To a stirred solution of III (B=—X—R$_3$; X=O; R$_3$=n-pentyl; R$_6$=hydrogen) (9.3 g, 0.035 moles) and dihydropyran (3.4 g, 0.039 moles) in dry benzene (100 ml) a solution of p-toluenesulfonic acid (60 mg) in dry benzene (20 ml) is added.

After 40 minutes the reaction mixture is poured into a bicarbonate solution and extracted twice with methylene chloride.

After drying (MgSO$_4$) the solvent is evaporated in vacuo leaving the title compound as an oil (12.4 g, quantitative yield).

Analysis for C$_{18}$H$_{29}$NO$_6$. Calc. C, 60.82; H, 8.22; N, 3.94. Found C, 60.65; H, 8.23; N, 3.87.

I.R. (neat): 3330, 1780, 1715, 1530 (cm$^{-1}$).

N.M.R. (CDCl$_3$), δ values=0.90 (t, J=5.5 Hz); 1.1–2.0 (m); 2.1–2.4 (m); 2.6–3.1 (m); 3.3–4.3 (m); 4.03 (t, J=6 Hz); 4.66 (d); 4.8–5.4 (m).

EXAMPLE 6

Transformation of III (B=—X—R$_3$; X=O; R$_3$=n-pentyl; R$_6$=tetrahydropyran-2-yl) to the corresponding lactol To a stirred solution of III (B=—X—R$_3$; X=O; R$_3$=n-pentyl; R$_6$=tetrahydropyran-2-yl) (12.4 g, 0.035 moles) in dry tetrahydrofuran (500 ml) cooled to −78° C. a solution of sodium bis-methoxyethoxy aluminium hydride (70% in benzene, 70 ml) diluted with dry tetrahydrofuran (150 ml) is added dropwise during three hours.

After one hour the reaction is over. A solution of methanol (50 ml) in dry tetrahydrofuran (70 ml) is then added dropwise in two hours at −78° C.

The reaction mixture is then poured into a potassium sodium tartrate solution.

After two extractions with ethyl acetate the combined extracts are washed with brine, dried (MgSO$_4$) and the solvent evaporated in vacuo giving 12.4 g. of practically pure lactol.

I.R. (neat): 3400–3300, 1700, 1530 (cm$^{-1}$)

N.M.R. (CDCl$_3$), δ values: 0.90 (t, J=5.5 Hz); 1.1–2.9 (m); 3.3–4.3 (m); 4.11 (t, J=6 Hz); 4.5–5.0 (m); 5.5 (d); 5.5–5.8 (m);

Analysis for C$_{18}$H$_{31}$NO$_6$. Calc. C, 60.48 H, 8.74 N, 3.92. Found C, 60.61 H, 8.90 N, 3.89.

EXAMPLE 7

Preparation of I(a) (B=—X—R$_3$; X=O; R, R$_2$=hydrogen; R$_1$=tetrahydropyran-2-yl; R$_3$=n-pentyl; A=cis-CH=CH—)

Sodium hydride (20.1 g, 0.407 moles, 55% in oil) is reacted at 70° C. with dry dimethylsulfoxide (200 ml) until hydrogen evolution ceases (90 minutes). The reaction mixture is cooled to 20° C. and (4-carboxybutyl) triphenylphosphonium bromide (101.5 g, 0.23 moles) is added in portions. After 15 minutes a solution of the previously described lactol (12.4 g, 0.035 moles) is added dropwise to the deep red solution at 25° C. After 100 minutes the reaction mixture is poured into icy water and extracted twice with methylene chloride to remove neutral compounds. The aqueous phase is then acidified with sodium dihydrogen phosphate and extracted with three portions of ethyl acetate (500 ml each). The combined extracts are washed twice with water, dried (MgSO$_4$) and the solvent evaporated. The residue is then left in ethyl acetate for one hour. Filtration then removes the solid (4-carboxybutyl)diphenylphosphine oxide.

The ethyl acetate solution is then evaporated and the residue (13 g) purified by column chromatography on acid washed silica gel (250 g) eluting with increasing proportions of ethyl ether in hexane; 8.6 g of I(a) are thus obtained. Yield 59%.

Analysis for C$_{23}$H$_{39}$NO$_7$. Calc. C, 62.56; H, 8.90; N, 3.17. Found C, 62.40; H, 8.86; N, 3.15.

I.R. (neat): 2400–3500, 3330, 1700, 1530 (cm$^{-1}$)

N.M.R. (CDCl$_3$), δ values: 0.9 (t, J=5.5 Hz); 1.1–2.5 (m); 3.2–4.2 (m); 4.05 (t, J=6 Hz); 4.4–5.3 (m); 5.2–5.5 (m).

EXAMPLE 8

Preparation of I(a) (B=—X—R$_3$; X=O; R, R$_1$, R$_2$=hydrogen; R$_3$=n-pentyl; A=cis-CH=CH—)

A solution of I(a) (B=—X—R$_3$; X=O; R, R$_2$=hydrogen; R$_1$=tetrahydropyran-2-yl; R$_3$=n-pentyl; A=cis-CH=CH—) (400 mg, 0.91 m moles) in acetone (18 ml) and HCl 1 N (3 ml) is kept at 40° C. for three hours.

The reaction mixture is then poured into brine and extracted twice with ethyl acetate. The combined extracts are washed with a solution of sodium dihydrogen citrate, then with brine, dried (MgSO$_4$) and the solvent evaporated in vacuo. The residue (350 mg) is purified by chromatography on 8 g. of acid-washed silica gel eluting with ethyl ether; 255 mg of the title product are thus obtained; yield 79%. M.P. 69° C. (crystallized from ethyl ether-petroleum ether).

$[\alpha]_D^{25} = +52$ (C=0.94%, chloroform)

Analysis for $C_{18}H_{31}NO_6$. Calc. C, 60.48; H, 8.74; N, 3.92. Found C, 60.67; H, 8.91; N, 3.90.

I.R. $(CDCl_3)$: 3440, 2400–3500, 1710, 1510 $(cm^{-1})$.

EXAMPLE 9

Preparation of I(b) (B=—X—$R_3$; X=O; $R_1$=tetrahydropyran-2-yl; $R_2$=hydrogen; $R_3$=n-pentyl; A=cis-CH=CH—)

To a stirred solution of I(a) (B=—X—$R_3$; X=O; R, $R_2$=hydrogen; $R_1$=tetrahydropyran-2-yl; $R_3$=n-pentyl; A=cis-CH=CH—) (1.2 g, 2.72 m moles) in ether (10 ml) kept at $-13°$ C. is added dropwise a cooled solution of $Na_2Cr_2O_7 2H_2O$ (0.8 g) in sulphuric acid (1.09 g) and water (4 ml).

After three hours at $-13°$ C. the reaction mixture is poured into an icy solution of sodium hydrogen phosphate dodecahydrate (10 g) and sodium dihydrogen phosphate (5 g).

After 3 extractions with ether, the combined extracts are washed with water, dried ($MgSO_4$) and the solvent removed in vacuo giving the title product (1 g) contaminated by traces of starting material.

Chromatography on acid washed silica gel by eluting with ether-hexane 60:40 affords 900 mg of pure product; yield 76%.

Analysis for $C_{23}H_{37}NO_7$. Calc. C, 62.85; H, 8.49; N, 3.19. Found C, 62.73; H, 8.51; N, 3.13.

I.R. (neat): 2400–3500, 3330, 1710, 1530 $(cm^{-1})$

N.M.R. $(CDCl_3)$, δ values: 0.90 (t, J=5.5 Hz); 1.1.–3.1 (m); 3.3–5.0 (m); 4.05 (t); 5.2–5.6 (m); 6.8–7.3 (m).

EXAMPLE 10

Preparation of I(b) (B=—X—$R_3$; X=O; $R_1$, $R_2$=hydrogen; $R_3$=n-pentyl; A=cis-CH=CH—)

A solution of I(b) (B=—X—$R_3$; X=O; $R_1$=tetrahydropyran-2-yl; $R_2$=hydrogen; $R_3$=n-pentyl; A=cis-CH=CH—) (1.5 g, 3.42 m moles) in acetone (40 ml) and 0, 1 N oxalic acid (20 ml) is kept at 45° C. for 24 hours.

The reaction mixture is then poured into water and extracted twice with ether. The combined extracts are washed with water, dried ($MgSO_4$) and the solvent evaporated in vacuo.

The residue is purified by chromatography on acid washed silica gel (40 g) using ether-hexane as the eluent. Yield 930 mg of the title compound (77%).

Analysis for $C_{18}H_{29}NO_6$. Calc. C, 60.82; H, 8.22; N, 3.94. Found C, 60.53; H, 8.43; N, 3.85.

$[\alpha]_D^{25} = -48.7$ (C=0.82%, chloroform).

I.R. $(CDCl_3)$: 3440, 2400–3500, 1750, 1710, 1510 $(cm^{-1})$

N.M.R. $(CDCl_3)$, δ values 0.9 (t, J=5.5 Hz); 1.2–3.2 (m); 3.5–4.6 (m); 4.06 (t, J=6 Hz); 5.2–6.0 (m); 6.3–7.2 (m).

EXAMPLE 11

Preparation of I(c) (B=—X—$R_3$; X=O; $R_2$=hydrogen; $R_3$=n-pentyl; A=cis-CH=CH—)

A solution of I(b) (B=—X—$R_3$; X=O; $R_1$=tetrahydropyran-2-yl; $R_2$=hydrogen $R_3$=n-pentyl; A=cis-CH=CH—) (1 g, 2.3 m moles) in acetone (30 ml) and 1 N HCl (5 ml) is kept at 40° C. for 2 hours. The solution is then poured into water and extracted twice with ethyl ether. The combined extracts are washed with water, dried ($MgSO_4$) and the solvent removed in vacuo.

The residue is purified by chromatography on acid washed silica gel using ether-hexane (6:4) as the eluent. Yield 660 mg (86%) of the title compound.

Analysis for $C_{18}H_{27}NO_5$. Calc. C, 64.07; H, 8.06; N, 4.15. Found C, 63.82; H, 7.99; N, 3.92.

$[\alpha]_D^{20} = +47.2$ (C=0.91%, chloroform)

I.R. $(CDCl_3)$ 3440, 2400–3500, 1710, 1510. $(cm^{-1})$

N.M.R. $(CDCl_3)$, δ values 0.90 (t, J=5.5 Hz); 1.1–2.8 (m); 4.06 (t, J=6 Hz); 4.4–4.8 (m); 4.9–5.6 (m); 6.16 (doublet of doublets, J=6 Hz, J=2 Hz); 7.45 (doublet of doublets, J=2 Hz); 6.5–7.0 (m).

EXAMPLE 12–15

The following compounds were prepared according to the same procedure of Examples 3 to 7.

(12) III (B=—X—$R_3$; X=O; $R_3$=tert-butyl; $R_6$=acetyl)

M.P. 123° C. (from ether).

$[\alpha]_D^{25} = -28.7$ (C=0.976%, chloroform).

Analysis for $C_{14}H_{21}NO_6$. Calc. C, 56.17; H, 7.07; N, 4.68. Found C, 56.18; H, 7.11; N, 4.72.

(13) III (B=—X—$R_3$; X=O; $R_3$=tert-butyl; $R_6$=hydrogen)

M.P. 157° C. (crystallized from ethyl acetate)

$[\alpha]_D^{25} = -7.4$ (C=1.075% ethanol)

Analysis for $C_{12}H_{19}NO_5$. Calc. C, 56.02; H, 7.44; N, 5.44. Found C, 56.19; H, 7.60; N, 5.57.

(14) III (B=—X—$R_3$; X=O; $R_3$=tert-butyl; $R_6$=tetrahydropyran-2-yl)

M.P. 93° C. (crystallized from ether-hexane)

Analysis for $C_{17}H_{27}NO_6$. Calc. C, 59.81; H, 7.97; N, 4.10. Found C, 59.88; H, 7.94; N, 4.21.

The corresponding lactol has m.p. 102°–104° C. (crystallized from ether-petroleum ether).

Analysis for $C_{17}H_{29}NO_6$. Calc. C, 59.45; H, 8.51; N, 4.08. Found C, 59.65; H, 8.47; N, 4.15.

(15) I(a) (B=—X—$R_3$; X=O; R, $R_2$=hydrogen; $R_1$=tetrahydropyran-2-yl; $R_3$=tert-butyl; A=cis-CH=CH—)

I.R. (neat): 3350, 2500–3500, 1700, 1530 $(cm^{-1})$

Analysis for $C_{22}H_{37}NO_7$. Calc. C, 61.80; H, 8.72; N, 3.28. Found C, 62.03; H, 8.90; N, 3.22.

N.M.R. $(CDCl_3)$, δ values: 1.1–2.6 (m); 1.45 (s); 3.1–4.3 (m); 4.4–5.2 (m); 5.3–5.6 (m); 5.9–6.9 (m).

EXAMPLE 16

Preparation of I(a) (B=—X—$R_3$; X=O; R=acetyl; $R_1$=tetrahydropyran-2-yl; $R_2$=methyl; $R_3$=tert-butyl; A=cis-CH=CH—)

I(a) (B=—X—$R_3$; X=O; $R_2$=hydrogen; $R_1$=tetrahydropyran-2-yl; $R_3$=tert-butyl; A=cis-CH=CH—) (427 mg, 1 m mole), dissolved in ether (15 ml) is treated with a small excess of a solution of diazomethane in ethyl ether. After 10 minutes the solvent is evaporated and the residue is dissolved in a solution of pyridine (1 ml) and acetic anhydride (0.5 ml).

After 24 hours at 50° C. the reaction mixture is poured in water and stirred for one hour. After two extractions with dichloromethane the combined extracts are washed with a bicarbonate solution and then with water. After drying ($MgSO_4$) the solvent is evaporated and the residue crystallized from ether-hexane. Yield 405 mg (84%). M.P. 86°–88° C.

Analysis for $C_{25}H_{41}NO_8$. Calc. C, 62.09; H, 8.55; N, 2.90. Found C, 62.19; H, 8.70; N, 2.84.

I.R. (nujol): 3390, 1735, 1695, 1525 (cm$^{-1}$).

EXAMPLE 17

Preparation of III (B=—X—$R_3$; X=NH; $R_3$=n-pentyl; $R_6$=acetyl)

To a solution of II ($R_6$=acetyl) (225 mg, 1 m mole) in dry benzene (10 ml) is added n-pentylamine (90 mg, 1.03 m moles) in dry benzene (5 ml). After one hour the solvent is removed in vacuo yielding the title compound as an oil (280 mg, 90% yield).

I.R. (neat): 3350, 1770, 1750, 1650, 1560 (cm$^{-1}$)

$[\alpha]_D^{25} = -16.4$ (C=1.83%, chloroform)

Analysis for $C_{15}H_{24}N_2O_5$. Calc. C, 57.67; H, 7.74; N, 8.97. Found C, 57.25; H, 7.62; N, 8.62.

EXAMPLE 18

Preparation of III (B=—X—$R_3$; X=NH; $R_3$=n-pentyl, $R_6$=hydrogen)

To a solution of III (B=—X—$R_3$; X=NH; $R_3$=n-pentyl; $R_6$=acetyl) (280 mg, 0.9 m moles) in methanol (10 ml) potassium carbonate (50 mg) is added. After 15 minutes citric acid (76 mg) is added and most of the solvent is removed in vacuo. The residue is diluted with brine and extracted three times with ethyl acetate. The combined extracts are dried (MgSO$_4$) and the solvent evaporated. The reaction is crystallized from ethyl acetate yielding 195 mg (80%) of the title compound. M.P. 136°–8° C.

$[\alpha]_D^{25} = -7.6$ (C=1.046% ethanol)

Analysis for $C_{13}H_{22}N_2O_4$. Calc. C, 57.76; H, 8.20; N, 10.36. Found C, 57.80; H, 8.33; N, 10.18.

EXAMPLE 19

Preparation of III (B=—X—$R_3$; X=NH; $R_3$=n-pentyl; $R_6$=tetrahydropyran-2-yl)

To a solution of III (B=—X—$R_3$; X=NH; $R_3$=n-pentyl; $R_6$=hydrogen) (4 g, 14.8 m moles) and dihydropyrane (7.5 g, excess) in dry tetrahydrofurane (100 ml) a solution of anhydrous p-toluensulphonic acid (50 mg) is added. After 4 hours the solution is poured into a sodium bicarbonate solution. The aqueous layer is then twice extracted with dichloromethane. The combined extract are dried (MgSO$_4$) and the solvent evaporated in vacuo. The residue (6 g) is purified by chromatography on silica gel using ethyl ether as the eluent. 4.2 Grams of the title compound are thus obtained. M.P. 117° C. (crystallized from ether).

Analysis for $C_{18}H_{30}N_2O_5$. Calc. C, 60.99; H, 8.53; N, 7.90. Found C, 60.80; H, 8.61 N, 7.82.

EXAMPLE 20

Transformation of III (B=—X—$R_3$; X=NH; $R_3$=n-pentyl; $R_6$=tetrahydropyran-2-yl) into the corresponding lactol.

To a stirred solution of III (B=—X—$R_3$; X=NH; $R_3$=n-pentyl; $R_6$=tetrahydropyran-2-yl) (0.5 g, 1.85 m moles) in dry tetrahydrofuran (50 ml) at −78° C., a solution of sodium bis methoxyethoxy aluminium hydride (70% in benzene, 12 ml) diluted with dry tetrahydrofuran (25 ml) is added dropwise on keeping the temperature below −70° C.

After four hours, methanol (7 ml) in tetrahydrofuran (20 ml) is added dropwise at −78° C. to destroy the reducing agent excess.

The reaction mixture is poured into a sodium potassium tartrate solution and the aqueous phase extracted twice with benzene. The combined extracts are washed with brine, dried (MgSO$_4$) and the solvent is removed in vacuo to yield the lactol (0.5 g).

This material being unstable is used without any further purification.

I.R. (neat): 3330, 1650, 1560 (cm$^1$)

N.M.R. (CDCl$_3$), δ values: 0.90 (t, J=5.5 Hz); 1.1–2.9 (m); 4.3–5.1 (m); 5.44 (t, J=6 Hz); 5.4–5.7 (m).

EXAMPLE 21

Preparation of I(a) (B=—X—$R_3$; X=NH; R, $R_2$=hydrogen; $R_1$=tetrahydropyran-2-yl; $R_3$=n-pentyl; A=cis-CH═CH—)

Sodium hydride (0.7 g, 55% dispersion in oil, 17.9 m moles) is reacted at 70° C. with dry dimethyl sulfoxide (10 ml) for 2 hours. After cooling to room temperature (4-carboxy-butyl)triphenyl phosphonium bromide (4.5 g, 10.1 m moles) is added in portions. After 15 minutes the lactol of Example 20 (0.5 g) in dry dimethyl sulfoxide (5 ml) is added at room temperature. After three hours the reaction mixture is poured into icy water and extracted twice with methylene chloride to remove neutral compounds. The aqueous phase is then acidified with sodium dihydrogen phosphate and extracted three times with ether. The combined extracts are washed with water, dried (MgSO$_4$) and the solvent evaporated in vacuo. The residue is left in ethyl acetate for one hour and then the solid (4-carboxy-butyl) diphenyl phosphine oxide is removed by filtration. The ethyl acetate solution is evaporated in vacuo and the residue (0.6 g) purified by chromatography on acid washed silica gel.

Elution with ether affords 430 mg. (76%) of the title compound. M.P. 85° C. (crystallized from ether).

Analysis for $C_{23}H_{40}N_2O_6$. Calc. C, 62.70; H, 9.15; N, 6.36. Found C, 62.84; H, 9.19; N, 6.32.

EXAMPLE 22

Preparation of I(b) (B=—X—$R_3$; X=NH; $R_1$=tetrahydropyran-2-yl; $R_2$=hydrogen; $R_3$=n-pentyl; A=cis-CH═CH—)

To a stirred solution of anhydrous pyridine (0.44 ml) in anhydrous methylene chloride (7 ml), anhydrous chromium trioxide (0.273) is added. After 15 minutes a solution of I(a) (B=—X—$R_3$; X=NH; R, $R_2$=hydrogen, $R_1$=tetrahydropyan-2-yl; $R_3$=n-pentyl; A=cis-CH═CH—) (100 mg) in anhydrous methylene chloride (3 ml) is added dropwise. After one hour ethyl acetate (80 ml) is added and the resulting slurry is filtered on celite.

The solution is then washed twice with water, dried (MgSO$_4$) and the solvent evaporated. The residue (120 mg) is purified by chromatography on acid washed silica gel eluting with ether. 60 mg are thus obtained. Yield 60%.

I.R. (neat): 3330, 2400, 3500, 1740, 1650, 1570 (cm$^{-1}$)

N.M.R. (CDCl$_3$), δ values: 0.90 (t, J=5.5 Hz); 1.1–2.9 (m); 3.0–4.5 (m); 4.9–5.8 (m); 7.8–8.8 (m).

EXAMPLE 23

Preparation of I(a) (B=—X—$R_3$; X=NH; R, $R_1$, $R_2$=hydrogen; $R_3$=n-pentyl A=cis-CH═CH—)

A solution of I(a) (B=—X—$R_3$; X=NH; R, $R_2$=hydrogen, $R_1$=tetrahydropyran-2-yl; $R_3$=n-pentyl; A=-cis-CH═CH—) (100 mg) in acetone (5 ml) and HCl 1 N (2 ml) is kept at 40° C. for three hours. The reaction mixture is then poured into brine and extracted twice with ethyl acetate. The combined extracts are washed with brine, dried (MgSO$_4$) and the solvent evaporated in vacuo. The residue is purified by chromatography on acid washed silica gel eluting with ethyl acetate. 54 mg are thus obtained. Yield 68%.

I.R. (CDCl$_3$): 3400, 2400, 3500, 1720, 1640, 1570 (cm$^{-1}$)

Analysis for C$_{18}$H$_{32}$N$_2$O$_5$. Calc. C, 60.65; H, 9.05; N, 7.86. Found C, 60.38; H, 8.97; N, 8.01.

N.M.R. (CDCl$_3$), δ values: 0.90 (t, J=5.5 Hz); 1.1–2.9 (m); 3.0–4.5 (m); 4.16 (d, J=7 Hz); 5.2–5.7 (m); 5.4–7.0 (m).

EXAMPLE 24

Preparation of I(b) (B=—X—R$_3$; X=NH; R$_1$, R$_2$=hydrogen; R$_3$=n-pentyl; A=cis-CH=CH—)

A solution of I(b) (B=—X—R$_3$; X=NH; R$_1$=tetrahydropyran-2-yl; R$_2$=hydrogen; R$_3$=n-pentyl; A=-cis-CH=CH—) (150 mg) in acetone (10 ml) and 0.1 N oxalic acid (4 ml) is kept at 50° C. After 30 hours the reaction mixture is poured into brine and extracted twice with ethyl acetate. The combined extracts are washed with water, dried (MgSO$_4$) and the solvent evaporated in vacuo. The due (155 mg) is purified by chromatography on acid washed silica gel using ethyl ether as the eluent yielding 87 mg (70%) of the title compound. I.R. (CDCl$_3$): 3400, 2400–3500, 1750, 1710, 1650, 1560 (cm$^{-1}$)

Analysis for C$_{18}$H$_{30}$N$_2$O$_5$. Calc. C, 60.99; H, 8.53; N, 7.90. Found C, 61.12; H, 8.39; N, 7.79.

N.M.R. (CDCl$_3$), δ values: 0.90 (t, J=5.5 Hz); 1.1–2.8 (m); 2.9–4.5 (m); 4.7–5.1 (m); 5.3–5.6 (m); 5.6–7.0 (m).

EXAMPLE 25

Preparation of III (B=—W—R$_3$; W=>CHO-acetyl; R$_3$=n-pentyl; R$_6$=acetyl)

A solution of 2-oxa-6-isocyanato-7-acetoxy-bicyclo [3.3.0]-octane-3-one (6 g) in a mixture of anhydrous benzene (20 ml) and pyridine (35 ml) was refluxed with α-acetoxy-heptanoic acid (8 gr). After three hours 30 ml of solvent were distilled, the reaction mixture was diluted with water, and extracted with dichloromethane. The organic phase was washed with 10% sulfuric acid, with saturated sodium bicarbonate, and finally with water. After drying (MgSO$_4$) the solvent was concentrated under vacuo and the residue chromatographed on silica gel. The title compound was eluted with ethyl acetate-hexane (1:1). After crystallization from ethyl ether-petroleum ether, the compound melts at 81°-83° C.

Analysis for C$_{18}$H$_{27}$NO$_7$. Calc. C, 58.52; H, 7.37; N, 3.79. Found C, 58.66; H, 7.45; N, 3.76.

I.R. (neat): 3300, 1780, 1740, 1670, 1550 (cm$^{-1}$)

EXAMPLE 26

Preparation of III (B=—W—R$_3$; W=>CHOH; R$_3$=n-pentyl; R$_6$=hydrogen).

A solution of III (B=—W—R$_3$; W=>CHO-acetyl; R$_3$=n-pentyl; R$_6$=acetyl) (18 gr, 49 m moles) in methanol (350 ml) was treated with anhydrous potassium carbonate (3 g) for 20 minutes. The reaction mixture was neutralized with a solution of citric acid in water (4 gr in 50 ml).

After evaporation of the methanol, the reaction mixture was diluted with a saturated ammonium sulfate solution (100 ml) and extracted 3 times with ethyl acetate. After drying (MgSO$_4$) the solvent was concentrated in vacuo and the residue (12.6 g) was chromatographed on silica gel. The title compound was eluted with ethyl acetate-hexane (5:5).

Analysis for C$_{14}$H$_{23}$NO$_5$. Calc. C, 58.93; H, 8.13; N, 4.91. Found C, 58.45; H, 8.23; N, 4.88.

I.R. (neat): 3300–3400, 1770, 1660, 1540 (cm$^1$)

N.M.R. (CDCl$_3$—DMSO), δ values: 0.90 (t, J=5.5 Hz); 1.1–2.0 (m); 2.0–2.5 (m); 2.5–3.0 (m); 3.7–4.3 (m); 4.6–4.8 (m); 4.8–5.2 (m); 7.29 (d).

EXAMPLE 27

Preparation of III (B=—W—R$_3$; W=>CHO-tetrahydropyran-2-yl; R$_3$=n-pentyl; R$_6$=tetrahydropyran-2-yl)

A solution of III (B=—W—R$_3$; W=>CHOH; R$_3$=n-pentyl; R$_6$=hydrogen) (12.6 gr. 44 m moles) in anhydrous tetrahydrofuran (100 ml) was treated with dihydropyran (10 ml) and anhydrous p-toluensulfonic acid (50 mg). After 45 minutes the reaction mixture was diluted with a saturated sodium bicarbonate solution under vigorous stirring and extracted twice with dichloromethane. After drying (MgSO$_4$) the solvent was concentrated under vacuo and the residue was azeotropically dried with benzene. The title compound was chromatographed on a silica gel column eluting with a mixture of ethyl ether and hexane.

Analysis for C$_{24}$H$_{39}$NO$_7$. Calc. C, 63.55; H, 8.67; N, 3.09. Found C, 63.08; H, 8.80; N, 2.90.

I.R. (neat): 3300, 1770, 1660, 1560 (cm$^{-1}$)

N.M.R. (CDCl$_3$), δ values: 0.90 (t, J=5.5 Hz); 1.1–2.0 (m); 2.1–2.4 (m); 2.8–3.2 (m); 3.4–4.4 (m); 4.5–5.4 (m); 6.3–7.2 (m).

EXAMPLE 28

Transformation of III (B=—W—R$_3$; W=>CHO-tetrahydropyran-2-yl; R$_3$=n-pentyl; R$_6$=tetrahydropyran-2-yl) into the corresponding lactol To a solution of the lactone III (B=—W—R$_3$; W=>CHO-tetrahydropyran-2-yl; R$_3$=n-pentyl; R$_6$=tetrahydropyran-2-yl) (19 gr) in anhydrous tetrahydrofuran (500 ml) cooled at −78° C., a solution of sodium bis (2-methoxyethoxy) aluminium hydride (120 ml 70% benzene solution) in anhydrous tetrahydrofuran (250 ml) was added dropwise. After 4 hours the excess of the reducing agent was cautiously destroyed by addition of methanol. The reaction mixture was diluted with a 1 M solution of sodium citrate. (1 l.) and extracted with benzene.

The organic phase, washed with brine (100 ml) and dried (MgSO$_4$) was concentrated under vacuo to give (19 g) of the title compound.

Analysis for C$_{24}$H$_{41}$NO$_7$. Calc. C, 63.27; H, 9.07; N, 3.07. Found C, 63.15; H, 9.11; N, 3.02.

I.R. (neat): 3350–3450, 1670, 1540 (cm$^{-1}$)

N.M.R. (CDCl$_3$), δ values: 0.89 (t); 1.1–2.9 (m); 3.3–4.4 (m); 4.5–5.0 (m); 5.5–5.8 (m); 6.4–7.4 (m).

EXAMPLE 29

Preparation of I(a) (B=—W—R$_3$;
W=>CHO-tetrahydropyran-2-yl; R, R$_2$=hydrogen;
R$_1$=tetrahydropyran-2-yl; R$_3$=n-pentyl;
A=cis-CH=CH—)

To a suspension of sodium hydride (30.15 g, 628 m moles), washed with anhydrous hexane, anhydrous dimethylsulfoxide (280 ml) was added and the reaction mixture was heated at 70° C. for 60 minutes. The dimethylsulfoxide anion solution was cooled to 20° C., treated with (4-carboxybutyl) triphenylphosphonium bromide (152 g) and to the resulting solution was added the lactol of Example 28 in dimethylsulfoxide (19 g in 25 ml).

After stirring for 3 hours at 26° C., the reaction mixture was diluted with cold water (1 liter) and extracted 3 times with ethyl acetate (500 ml each time) to remove neutral compounds. The aqueous solution was acidified to pH 4 with a saturated NaH$_2$PO$_4$ solution and extracted 3 times with ethyl acetate (500 ml each time). The organic phase washed twice with water (100 ml each time) was dried (MgSO$_4$) and concentrated in vacuo to 300 ml. The solid precipitate was filtered off and the solution concentrated in vacuo to give 16 g of the title compound.

The compound was purified through chromatography on silica gel (300 g) using ethyl ether as the eluent.

I.R. (neat): 3300, 2400–3500, 1730, 1660, 1540 (cm$^{-1}$)

N.M.R. (CDCl$_3$), δ values: 0.89 (t, J=5.5 Hz); 1.1–2.5 (m); 3.2–4.3 (m); 4.4–5.0 (m); 5.1–6.0 (m); 6.3–7.1 (m).

Analysis for C$_{29}$H$_{49}$NO$_8$. Calc. C, 64.54; H, 9.15; N, 2.60. Found C, 64.78; H, 9.21; N, 2.56.

EXAMPLE 30

Preparation of I(a) (B=—W—R$_3$; W=>CHOH;
R,R$_1$,R$_2$=hydrogen; R$_3$=n-pentyl;
A=cis-CH=CH—).

To a solution of the compound of Example 29 (2 g) in acetone (20 ml), 1 N hydrochloric acid (10 ml) was added and the reaction maintained for 1 hour at 50° C. After dilution with brine, the reaction mixture was extracted with ethyl acetate and the organic phase washed with brine. After drying (MgSO$_4$) the solvent was concentrated under vacuo. Purification through chromatography gave two products in the same amount (300 mg). The two compounds are diastereoisomeric at the 15 position.

Analysis for C$_{19}$H$_{33}$NO$_6$ (The less polar compound). Calc. C, 61.43; H, 8.95; N, 3.77. Found C, 61.00; H, 9.00; N, 3.72.

[α]$_D^{25}$=+4.4 (C=1.12%, ethanol)

Analysis for C$_{19}$H$_{33}$NO$_6$ (The more polar compound). Calc. C, 61.43; H, 8.95; N, 3.77. Found C, 61.20; H, 9.05; N, 3.82.

[α]$_D^{25}$=+29.3 (C=1.04%, ethanol)

I.R. and N.M.R. spectra are the same for both isomers.

I.R. (CDCl$_3$): 3450, 2400–3600, 1730, 1655, 1530 (cm$^1$)

N.M.R. (CDCl$_3$), δ values: 0.90 (t, J=5.5 Hz); 1.1–2.6 (m); 3.4–4.3 (m); 5.1–5.9 (m); 7.1–7.4 (m).

EXAMPLE 31

Preparation of I(b) (B=—W—R$_3$;
W=>CHO-tetrahydropyran-2-yl;
R$_1$=tetrahydropyran-2-yl; R$_2$=hydrogen;
R$_3$=n-pentyl; A=cis-CH=CH—)

To a solution of Collins reagent (10 g) in anhydrous CH$_2$Cl$_2$ (70 ml) a solution of I(a) (B=—W—R$_3$; W=>CHO-tetrahydropyran-2-yl; R, R$_2$=hydrogen; R$_1$=tetrahydropyran-2-yl; R$_3$=n-pentyl; A=cis-CH=CH—) (3 g) in anhydrous CH$_2$Cl$_2$ (25 ml) was added. The reaction mixture was diluted with water and extracted with CH$_2$Cl$_2$. The dried solution (MgSO$_4$), was concentrated under vacuo and the reaction product purified by chromatography (on silica gel using ethyl ether as the eluent) to give 2.4 g of the title product.

I.R. (neat): 3300, 2500–3500, 1750, 1730, 1660, 1540 (cm$^{-1}$)

N.M.R. (CDCl$_3$), δ values: 0.90 (t, J=5.5 Hz); 1.1–2.9 (m); 3.2–4.7 (m); 5.2–5.5 (m); 6.5–7.3 (m); 7.4–8.0 (m).

Analysis for C$_{25}$H$_{47}$NO$_8$. Calc. C, 64.77; H, 8.81; N, 2.61. Found C, 64.82; H, 8.85; N, 2.55.

EXAMPLE 32

Preparation of I(b) (B=—W—R$_3$; W=>CHOH; R$_1$, R$_2$=hydrogen; R$_3$=n-pentyl; A=cis-CH=CH—).

To a solution of I(b) (B=—W—R$_3$; W=>CHO-tetrahydropyran-2-yl; R$_1$=tetrahydropyran-2-yl; R$_2$=hydrogen; R$_3$=n-pentyl; A=cis-CH=CH—) (1.98 g) in acetone (30 ml), a solution 0.1 N of oxalic acid (15 ml) was added and the reaction mixture was maintained at 50° C. for 3 hours. The acetone solution was diluted with brine and extracted with ethyl acetate. The dried solution was concentrated under vacuo and the residue chromatographed on an acid washed silica gel column eluting with ethyl ether-hexane (8:2), to give the two diastereoisomeric compounds at the 15 position.

The less polar compound was crystallized from acetone petroleum ether. M.P. 102°–103° C.

[α]$_D^{25}$=−70 (C=1.07%, ethanol)

The more polar compound (on TLC) was an oil with [α]$_D^{25}$=−36.6 (C=0.87%, chloroform)

I.R. and N.M.R. spectra are the same for both isomers.

I.R. (neat) 3370, 3200, 2400–3500, 1755, 1725, 1655, 1540 (cm$^1$)

N.M.R. (CDCl$_3$), δ values: 0.90 (t, J=5.5 Hz); 1.1–2.9 (m); 3.5–4.5 (m); 5.2–5.6 (m); 6.0–7.0 (m); 7.1–7.8 (m).

EXAMPLE 33

Preparation of I(c) (B=—W—R$_3$; W=>CHOH;
R$_2$=hydrogen; R$_3$=n-pentyl; A=cis-CH=CH—)

To a solution of I(b) (B=—W—R$_3$; W=>CHO-tetrahydropyran-2-yl; R$_1$=tetrahydropyran-2-yl; R$_2$=hydrogen; R$_3$=n-pentyl; A=cis-CH=CH—) (1.5 g) in acetone (40 ml), a solution 1 N of hydrochloric acid (10 ml) was added, and the reaction mixture was maintained at 50° C. for 7 hours.

The acetone solution was partially concentrated, diluted with water, and extracted with dichloromethane. The organic phase was washed with water and concentrated under vacuo. The residue was chromatographed on preparative thin layer chromatography (silica gel; eluent: cyclohexane-ethylacetate-acetic acid 60:40:3) to give the two diastereoisomeric compounds at the 15 position. The less polar compound has $[\alpha]_D^{25} = +30$ (C=0.9%, chloroform). The more polar compound has $[\alpha]_D^{25} = +55.7$ (C=0.97%, chloroform).

I.R. and N.M.R. are the same for the two isomers.

I.R. (neat): 3400, 2400–3600, 1718, 1675, 1600 (w), 1520 (cm$^{-1}$)

N.M.R. (CDCl$_3$), δ values: 0.90 (t, J=5.5 Hz); 1.0–2.8 (m); 4.0–4.3 (m); 4.6–5.2 (m); 5.2–5.7 (m); 5.8–6.6 (m); 6.3 (double of doublets, J=6 Hz); 7.2 (d, J=8 Hz); 7.54 (doublet of doublets, J=2 Hz).

EXAMPLE 34

Preparation of I(a) (B=—W—R$_3$;
W=—CHOH—(CH$_2$)$_m$—X—; m=1; X=O;
R,R$_1$,R$_2$=hydrogen; R$_3$=p-fluorophenyl;
A=cis-CH=CH—)

The compound of the title was prepared from 2-oxa-6-isocyanato-7-acetoxybicyclo[3.3.0]octane-3-one by following essentially the same procedures of examples 25 through 30. The reaction partner 3-(p-fluorophenoxy) lactic acid (m.p. 146° C.) was prepared according to the procedures described in U.S. Pat. No. 3,699,097. Before reaction with the isocyanate, the hydroxy group of the above lactic acid derivative was protected by acetylation.

The compound of the title consists of two diastereoisomers at the fifteen position easily separable by column chromatography on an acid washed silica gel using ethyl acetate-hexane 7:3 as the eluent.

The less polar isomer has the following characteristics:

Analysis for C$_{21}$H$_{28}$FNO$_7$. Calc. C, 59.28; H, 6.63; N, 3.29. Found C, 59.71; H, 6.45; N, 3.35.

$[\alpha]_D^{25} = 0$ (C=0.67%, ethanol)

The more polar isomer has the following characteristics:

Analysis for C$_{21}$H$_{28}$FNO$_7$. Calc. C, 59.28; H, 6.63; N, 3.29. Found C, 59.41; H, 6.55; N, 3.25.

$[\alpha]_D^{25} = +17.3$ (C=0.52%, ethanol)

The more polar isomer crystallizes from ethyl acetate-hexane. M.P. 114° C.

The I.R. and N.M.R. spectra are the same for the two isomers.

I.R. (neat): 3450, 2400–3550, 1710, 1650, 1540, 1505, 830 (cm$^{-1}$)

N.M.R. (CDCl$_3$-DMSO), δ values: 1.3–2.5 (m); 3.8–4.5 (m); 5.1–5.7 (m); 6.88–7.0 (m); 7.2–7.4 (d).

EXAMPLE 35

Preparation of I(a) (B=—W—R$_3$;
W=>CHNHCOO-tert-butyl; R,R$_2$=hydrogen;
R$_1$=tetrahydropyran-2-yl; R$_3$=n-pentyl;
A=cis-CH=CH—)

The compound of the title was prepared from 2-oxa-6-isocyanato-7-acetoxybicyclo[3.3.0]octane-3-one by following essentially the procedure of example 25 through 29.

The reaction partner 2-[N-(tert-butoxycarbonyl)amino]-heptanoic acid (m.p. 74° C.) was prepared from 2-aminoheptanoic acid and tert-butoxycarbonylazide.

EXAMPLE 36

Preparation of I(a) (B=—W—R$_3$; W=>CHNH$_2$;
R,R$_1$,R$_2$=hydrogen; R$_3$=n-pentyl;
A=cis-CH=CH—)

The compound of example 35 (0.5 g) was stirred for two hours with 90% trifluoro acetic acid at room temperature. The excess of acid was then evaporated and the residue purified by column chromatography on a polystyrene sulfonated resin (Amberlite CG-120) eluting first with water and then with increasing amounts of ammonia in water, to give the title compound (280 mg).

This compound consists of two diastereoisomers at the 15 position easily separable by TLC. (In butanol/acetic acid/water 4:1:1). The mixture of the two stereoisomers has the following characteristics:

I.R. (nujol): 2300–3550, 1670, 1520–1570 (cm$^{-1}$)

N.M.R. (DMSO), δ values: 0.90 (t, J=5.5 Hz); 1.1–1.8 (m) 1.8–2.4 (m); 3–3.6 (m); 3.6–4.1 (m); 4.5–5 (m); 5.15–5.5 (m); 7.7–8.1 (m).

Analysis for C$_{19}$H$_{34}$N$_2$O$_5$. Calc. C, 61.59; H, 9.25; N, 7.56. Found C, 61.78; H, 9.33; N, 7.44.

EXAMPLE 37

Preparation of I(a) (B=—W—R$_3$; W=>CHNH$_2$;
R,R$_1$,R$_2$=hydrogen; R$_3$=n-pentyl;
A=cis—CH$_2$—CH$_2$—)

The compound of example 36 (400 mg) dissolved in 50% ethanol was hydrogenated in the presence of 10% Palladium on carbon (100 mg). After three hours, absorption of gas ceases, the catalyst was filtered and the solvent removed to give the title compound (400 mg).

This compound consists of two diastereoisomers at the 15 position easily separable by TLC (n butanol/acetic acid/water 4:1:1).

The mixture of the two diastereoisomers has the following characteristics:

Analysis for C$_{19}$H$_{36}$N$_2$O$_5$. Calc. C, 61.26; H, 9.74; N, 7.52. Found C, 61.08; H, 9.61; N, 7.64.

I.R. (nujol): 3300, 2300–3600, 1670, 1540–1600 (cm$^{-1}$)

N.M.R. (DMSO), δ values: 0.90 (t, J=5.5 Hz); 1.05–1.8 (m); 1.95–2.35 (m); 3.05–3.4 (m); 3.6–4.1 (m), 7.55–7.85 (m).

The more polar isomer after crystallization from ethanol has the following characteristics: M.P. 216° C.

$[\alpha]_D^{25} = +13$ (C=0.38% 1 N HCl)

Analysis for C$_{19}$H$_{36}$N$_2$O$_5$. Calc. C, 61.26; H, 9.74; N, 7.52. Found C, 61.15; H, 9.86; N, 7.55.

The I.R. and N.M.R. are the same as before.

EXAMPLE 38

Preparation of I(a) (B=W—R$_3$;
W=—CHOH—(CH$_2$)$_m$-X—; m=1; X=O;
R,R$_1$,R$_2$=hydrogen; R$_3$=3,4-dimethylphenyl;
A=cis—CH=CH—)

The compound of the title was prepared from 2-oxa-6-isocyanato-7-acetoxy-bicyclo[3.3.0]octane-3-one by following essentially the same procedures of examples 25 through 30. The reaction partner 3-(3,4-dimethylphenoxy) lactic acid (m.p. 121° C.) was prepared according to the procedure described in U.S. Pat. No. 3,699,097. Before reaction with the isocyanate, the hydroxy group of the above lactic acid derivative was protected by acetilation. The compound of the title consists of two diastereoisomers at the 15 position easily separable by column chromatography on acid washed silica gel using ethylacetate-hexane 7:3 as the eluent.

The less polar isomer has the following characteristics.

Analysis for C$_{23}$H$_{33}$NO$_7$. Calc. C, 63.43; H, 7.64; N, 3.22. Found C, 63.35; H, 7.55; N, 3.20.

$[\alpha]_D^{25} = +6$ (C=1%, ethanol 95%).

M.p. 93°–96° C. (from ethyl acetate-hexane)

The more polar isomer has the following characteristics.

Analysis for $C_{23}H_{33}NO_7$. Calc. C, 63.43; H, 7.64; N, 3.22. Found C, 63.30; H, 7.79; N, 3.18.

$[\alpha]_D^{25} = +26$ (C=1%, ethanol 95%).

M.p. 131° C. (from ethyl acetate).

The I.R. and N.M.R. spectra are the same for the two isomers.

I.R. (nujol): 3480, 3400, 2300–3500, 1720, 1660, 1620, 1580, 1520 (cm$^{-1}$)

N.M.R. (CDCl$_3$-DMSO), δ values: 1.3–2.7 (m); 2.13 s); 2.16 (s); 3.7–4.5 (m); 4.4–6.1 (m); 5.2–5.5 (m); 6.49 d); 6.58 (s); 6.83 (d); 7.1–7.4 (m).

EXAMPLE 39

Preparation of I(a) (B=W—R$_3$;
W=—CHOH—(CH$_2$)$_m$—X—; m=1; X=O;
R,R$_1$,R$_2$=hydrogen; R$_3$=m-trifluoromethylphenyl;
A=cis-CH=CH—)

The compound of the title was prepared from 2-oxa-6-isocyanato-7-acetoxy-bicyclo[3.3.0]octane-3-one by following essentially the same procedures of examples 25 through 30. The reaction partner 3-(m-trifluoromethylphenoxy) lactic acid (m.p. 99° C.), was prepared according to the procedure described in U.S. Pat. No. 3,699,097. Before reaction with the isocyanate, the hydroxy group of the above lactic acid derivative was protected by acetilation. The compound of the title consists of two diastereoisomers at the 15 position easily separable by column chromatography on acid washed silica gel using ethyl acetate-hexane 7:3 as the eluent.

The less polar isomer has the following characteristics.

Analysis for $C_{22}H_{28}F_3NO_7$. Calc. C, 55.57; H, 5.94; N, 2.95. Found C, 55.66; H, 6.01; N, 2.87.

$[\alpha]_D^{25} = +27$ (C=1% ethanol)

The more polar isomer has the following characteristics:

Analysis for $C_{22}H_{28}F_3NO_7$. Calc. C, 55.57; H, 5.94; N, 2.95. Found C, 55.36; H, 5.88; N, 3.01.

$[\alpha]_D^{25} = +11$ (C=1% ethanol)

The I.R. and N.M.R. spectra are the same for the two isomers.

I.R. (neat): 3300, 2400–3600, 1710, 1650, 1580, 1540 cm$^{-1}$).

N.M.R. (CDCl$_3$—DMSO), δ values: 1.2–1.7 (m); 3.8–4.7 (m); 4.9–5.9 (m); 7.0–7.7 (m).

EXAMPLE 40

Preparation of I(a) (B=W—R$_3$; W=>CH-OCH$_3$;
R,R$_1$=hydrogen; R$_2$=methyl; R$_3$=n-pentyl;
A=cis-CH=CH—)

The compound of the title was prepared from 2-oxa-6-isocyanato-7-acetoxy-bicyclo[3.3.0]octane-3-one by following essentially the same procedures of examples 245 through 30. The reaction partner 2-methoxy-heptanoic acid (b.p. 100° C. at 18 mmHg) was prepared with standard procedures.

The compound of the title consists of two diastereoisomers at the 15 position easily separable by column chromatography on silica gel using methylene chloride-methanol 99/1 as the eluent.

The less polar isomer has the following characteristics;

Analysis for $C_{21}H_{37}NO_6$. Calc. C, 63.13; H, 9.33; N, 3.50. Found C, 63.38; H, 9.41; N, 3.41.

M;p. 53°–55° C. (from ether-hexane)

The more polar isomer has the following characteristics:

Analysis for $C_{21}H_{37}NO_6$. Calc. C, 63.13; H, 9.33; N, 3.50. Found C, 62.78; H, 9.26; N, 3.40.

M.p. 75°–77° (from ether-hexane)

$[\alpha]_D^{25} = +67.7$ (C=0.945% chloroform)

The I.R. and N.M.R. spectra are the same for the two isomers.

I.R. (neat): 3450, 3300, 1730, 1650, 1550 (cm$^{-1}$)

N.M.R. (CDCl$_3$), δ values: 0.88 (t); 1.2–2.8 (m); 3.4–4.7 (m); 3.40 (s); 3.67 (s); 5.2–5.8 (m); 6.74 (d).

By operating according to the procedures described before the following compounds are prepared.

| Structure of ring P | A | R | R$_1$ | R$_2$ | B |
|---|---|---|---|---|---|
| (a) | —CH=CH— | H | H | H | —NH—C$_6$H$_5$ |
| (a) | —CH=CH— | H | H | H | —NH-(p . Cl—C$_6$H$_4$) |
| (a) | —CH=CH— | H | H | H | —NH-(m . NO$_2$—C$_6$H$_4$) |
| (a) | —CH=CH— | H | H | H | —O-(m . CH$_3$O—C$_6$H$_4$) |
| (b) | —CH=CH— | H | H | H | —CHOH—CH$_2$—O-(p . CN—C$_6$H$_4$) |
| (b) | —CH$_2$—CH$_2$— | H | H | CH$_3$ | —CH$_2$—O-(m . CF$_3$—C$_6$H$_4$) |
| (b) | —Ch$_2$—CH$_2$— | H | H | H | —CHNH$_2$-(p . NO$_2$—C$_6$H$_4$) |
| (a) | —CH=CH— | H | H | H | —CHOH—CH$_2$—O-(p . Br—C$_6$H$_4$) |
| (a) | —CH$_2$—CH$_2$— | H | H | H | —CHNH$_2$-(o . Cl—C$_6$H$_4$) |
| (a) | —CH=CH— | H | H | H | —CHNH$_2$—C$_6$H$_5$ |
| (a) | —CH=CH— | H | H | Na | —CHOH-(m . F—C$_6$H$_4$) |
| (b) | —CH=CH— | H | H | H | —CHOH-(m . F—C$_6$H$_4$) |
| (a) | —CH=CH— | H | H | H | —CHOH—C$_6$H$_5$ |

We claim:

1. A compound of the formula

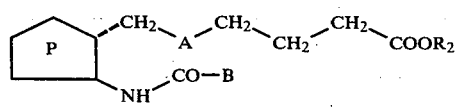

wherein the five-membered ring P represents

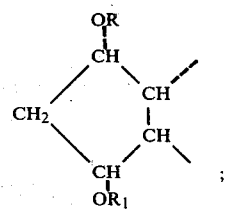

R, R$_1$ and R$_2$ each represents hydrogen; the symbol A represents cis-CH=CH—; and the symbol B represents —W—R$_3$ wherein W represents —CHOH-CH$_2$—O— and R$_3$ represents p-fluorophenyl.

* * * * *

UNITED STATES PATENT AND TRADEMARK OFFICE
CERTIFICATE OF CORRECTION

PATENT NO. : 4,189,606

DATED : February 19, 1980

INVENTOR(S) : Duccio Favara, et al.

It is certified that error appears in the above-identified patent and that said Letters Patent are hereby corrected as shown below:

Column 4, line 5, "to the common" should read --to common--.

Column 7, line 68, "drofuran" should read --hydrofuran--.

Column 10, line 4, "$C_{18}h_{27}NO_5$." should read --$C_{18}H_{27}NO_5$.--

Column 12, line 48, "$R_1$=tetrahydropyan-2-yl;" should read --$R_1$=tetrahydropyran-2-yl;--.

Column 20, line 9, "245" should read, --25--.

Column 20, line 26, "75°-77°" should read --75°-77° C.--.

Column 20, Claim 1, first formula should read --

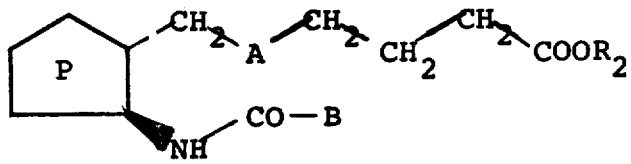

--.

UNITED STATES PATENT AND TRADEMARK OFFICE
CERTIFICATE OF CORRECTION

PATENT NO. : 4,189,606
DATED : February 19, 1980
INVENTOR(S) : Duccio Favara, et al.

It is certified that error appears in the above-identified patent and that said Letters Patent are hereby corrected as shown below:

Column 20, Claim 1, second formula, should read

--

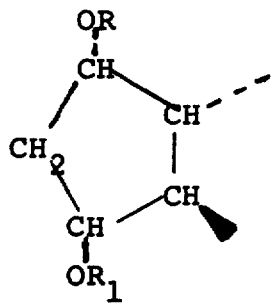

; --.

Signed and Sealed this

First Day of July 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,189,606
DATED : February 19, 1980
INVENTOR(S) : Duccio Favara, et al.

It is certified that error appears in the above—identified patent and that said Letters Patent is hereby corrected as shown below:

Column 20, Claim 1, first formula should read

--
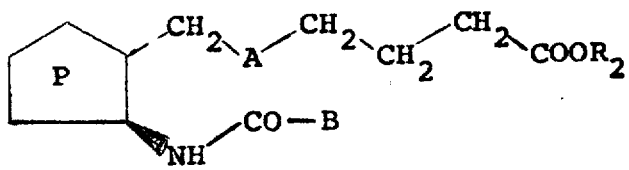

Column 20, Claim 1, second formula, should read

--
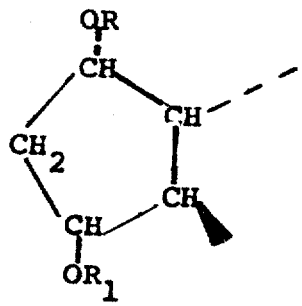

Signed and Sealed this

Fifth Day of August 1980

[SEAL]

Attest:

SIDNEY A. DIAMOND

Attesting Officer  Commissioner of Patents and Trademarks